(12) United States Patent
Andrews et al.

(10) Patent No.: US 11,006,923 B2
(45) Date of Patent: *May 18, 2021

(54) ULTRASONICALLY GUIDED BIOPSIES IN THREE DIMENSIONS

(71) Applicant: KONINKLIJKE PHILIPS N.V., Eindhoven (NL)

(72) Inventors: Gary Lee Andrews, Eindhoven (NL); Vijay Parthasarathy, Mount Kisco, NY (US); Gary Cheng-How Ng, Redmond, WA (US); Douglas Allen Stanton, Ossining, NY (US); Andrew Lee Robinson, Bellevue, WA (US); Jochen Kruecker, Washington, DC (US); Christopher Stephen Hall, Kirkland, WA (US); James Robertson Jago, Seattle, WA (US); Vijay Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1045 days.

This patent is subject to a terminal disclaimer.

(21) Appl. No.: 14/409,542

(22) PCT Filed: Jun. 28, 2013

(86) PCT No.: PCT/IB2013/055319
§ 371 (c)(1),
(2) Date: Dec. 19, 2014

(87) PCT Pub. No.: WO2014/002066
PCT Pub. Date: Jan. 3, 2014

(65) Prior Publication Data
US 2015/0320439 A1 Nov. 12, 2015

Related U.S. Application Data

(60) Provisional application No. 61/665,476, filed on Jun. 28, 2012.

(51) Int. Cl.
*A61B 8/00* (2006.01)
*A61B 8/08* (2006.01)
(Continued)

(52) U.S. Cl.
CPC .......... *A61B 8/0841* (2013.01); *A61B 8/4444* (2013.01); *A61B 8/4455* (2013.01);
(Continued)

(58) Field of Classification Search
CPC .......................... A61B 8/0833; A61B 17/3403
See application file for complete search history.

(56) References Cited

U.S. PATENT DOCUMENTS 5,255,682 A 10/1993 Pawluskiewicz et al.
5,758,650 A * 6/1998 Miller .................. A61B 8/0841
600/461
(Continued)

FOREIGN PATENT DOCUMENTS

CN 86205838 U 8/1987
CN 201701301 U 1/2011
(Continued)

OTHER PUBLICATIONS

"Enhancement of Needle Visibility in Ultrasound-Guided Percutaneous Procedures" Cheung et al, Ultrasound in Med & Biol. vol. 30, No. 5, pp. 617-624 (2004).

*Primary Examiner* — Joseph M Santos Rodriguez (57) ABSTRACT

An ultrasound system includes a 3D imaging probe and a needle guide which attaches to the probe for guidance of needle insertion into a volumetric region which can be scanned by the 3D imaging probe. The needle guide responds to the insertion of a needle through the guide by identifying a plane for scanning by the probe which is the insertion plane through which the needle will pass during insertion. The orientation of the insertion plane is commu-
(Continued)

nicated to the probe to cause the probe to scan the identified plane and produce images of the needle as it travels through the insertion plane.

20 Claims, 6 Drawing Sheets

(51) Int. Cl.
*A61B 17/34* (2006.01)
*A61B 90/00* (2016.01)

(52) U.S. Cl.
CPC .............. *A61B 8/483* (2013.01); *A61B 8/523* (2013.01); *A61B 8/56* (2013.01); *A61B 17/3403* (2013.01); *A61B 8/463* (2013.01); *A61B 2017/3413* (2013.01); *A61B 2090/0807* (2016.02)

(56) References Cited

U.S. PATENT DOCUMENTS

| | | | |
|---|---|---|---|
| 5,997,479 A | 12/1999 | Savord et al. | |
| 6,203,499 B1 | 3/2001 | Imling et al. | |
| 6,436,048 B1 | 4/2002 | Pesque | |
| 8,527,033 B1 * | 9/2013 | Williams | A61M 5/427 600/424 |
| 2004/0002653 A1 | 1/2004 | Greppi et al. | |
| 2004/0034297 A1 | 2/2004 | Darrow et al. | |
| 2005/0090742 A1 | 4/2005 | Mine | |
| 2006/0122628 A1 * | 6/2006 | Solar | A61B 90/11 606/130 |
| 2007/0179380 A1 | 8/2007 | Grossman | |
| 2009/0005687 A1 | 1/2009 | Kawae | |
| 2009/0171219 A1 | 7/2009 | Uchibori | |
| 2010/0063401 A1 | 5/2010 | Nishina et al. | |
| 2010/0240997 A1 | 9/2010 | Ichioka et al. | |
| 2010/0298704 A1 * | 11/2010 | Pelissier | A61B 8/0833 600/443 |
| 2010/0305432 A1 | 12/2010 | Duhay et al. | |

FOREIGN PATENT DOCUMENTS

| | | |
|---|---|---|
| CN | 202015250 U | 10/2011 |
| EP | 1958588 A2 | 8/2008 |
| JP | 2004305535 A | 11/2004 |
| JP | 2009118961 A | 6/2009 |
| JP | 2010068923 A | 4/2010 |
| WO | 2006060657 A2 | 6/2006 |
| WO | 2007110076 A1 | 10/2007 |
| WO | 2010125505 A1 | 11/2010 |
| WO | 2013108198 | 7/2013 |

* cited by examiner

ULTRASONICALLY GUIDED BIOPSIES IN THREE DIMENSIONS

This application is the U.S. National Phase application under 35 U.S.C. § 371 of International Application No. PCT/IB2013/055319, filed on Jun. 28, 2013, which claims the benefit of U.S. Provisional Application No. 61/665476 filed on Jun. 28, 2012. These applications are hereby incorporated by reference herein.

This invention relates to medical diagnostic ultrasound systems and, in particular, to ultrasonic diagnostic imaging systems which enable the visualization and guidance of biopsy needle insertion in real time.

Ultrasonic imaging has long been used to image the insertion path of biopsy needles and other invasive devices so that the clinician can visually observe the insertion of the needle toward and to target anatomy which is to be biopsied. Conventionally this is done with two dimensional (2D) ultrasound imaging and a 2D imaging probe equipped with a needle guide. One such needle guide is illustrated in U.S. Pat. No. 6,203,499 (Imling et al.) The purpose of the needle guide is to keep the needle in alignment with the plane of the 2D image of the ultrasound probe so that the insertion of the needle continuously takes place within that plane where it is continually imaged by the ultrasound probe. The needle guide clips onto the probe so that the hole or slot in the guide through which the needle is inserted is in fixed alignment with the image plane of the probe. This limits needle insertion to two positions, one end of the probe or the other. The clinician manipulates the probe until the target anatomy is in view in the image plane. The clinician then inserts the needle through the guide and at an inclination which will cause the tip of the needle to be inserted toward and access the target anatomy. A sample of the target anatomy can then be extracted through the lumen of the needle.

A difficulty commonly encountered in needle biopsies is keeping the insertion path of the needle constantly in alignment with the image plane of the probe. There are two sources of this difficulty. One is that the probe must be held stationary with one hand to keep the image plane in a fixed position while the needle is manipulated and inserted with the other hand. The other is that the needle can bend and deflect as it is inserted and encounters tissues of different density and stiffness as it penetrates the tissue of the body. This can cause the needle to vary from a single plane as it is inserted. Hence it would be desirable to have a wider field of of view of the target anatomy and the needle insertion path such as one afforded by three dimensional (3D) ultrasound imaging. It would further be desirable to enable the needle to be inserted from a variety of positions and not just from the ends of the probe.

Three dimensional ultrasound imaging will afford a wider field of view of the needle insertion. However, many clinicians do not like the clutter and often ambiguous perception of depth in a 3D ultrasonic imaging. They prefer a clear and easy to understand two dimensional image. One way to accommodate this desire is to use 3D imaging with multi-planar reconstruction (MPR). With MPR the 3D probe will scan the three dimensional volume in front of the probe which includes the target anatomy, then one plane in the volume is chosen to be constructed as a 2D image. This enables the clinician to hold the 3D probe stationary and adjust the MPR plane location to accommodate a changing needle insertion plane. Unfortunately, this is in practice a three-handed procedure: one hand to hold the probe, one to insert the needle, and a third to adjust the location of the MPR plane. It would be desirable to improve this procedure so that the needle will be continually imaged in a 3D volume with one hand holding the probe and the other inserting the needle.

In accordance with the principles of the present invention, a diagnostic ultrasound system has a 3D imaging probe with a needle guide that automatically aligns the plane of a displayed ultrasound image with the plane of needle insertion. A needle guide attached to the imaging probe produces a signal identifying the location of the plane of needle insertion in a volumetric region which can be scanned by the probe. The ultrasound system produces an image of the identified plane, preferably by biplane imaging by which only the identified plane or planes are scanned. In one embodiment the insertion planes of multiple needles can be identified, facilitating use of an ultrasound system of the present invention for procedures such as r.f ablation using multiple needles. In another embodiment the insertion planes of differently inclined needles can be identified and visualized.

Figure 1:
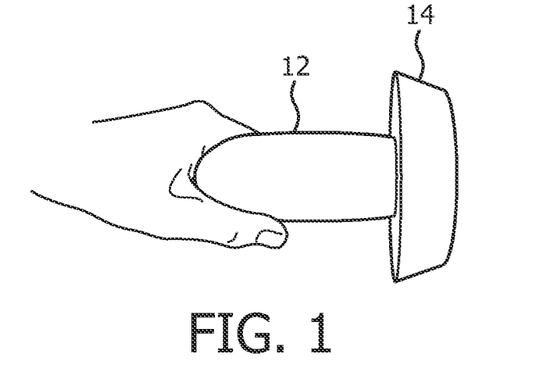
FIG. 1 illustrates a 3D ultrasound probe being held by the probe handle with a needle guide of the present invention attached to the distal end of the probe.
Figure 2:
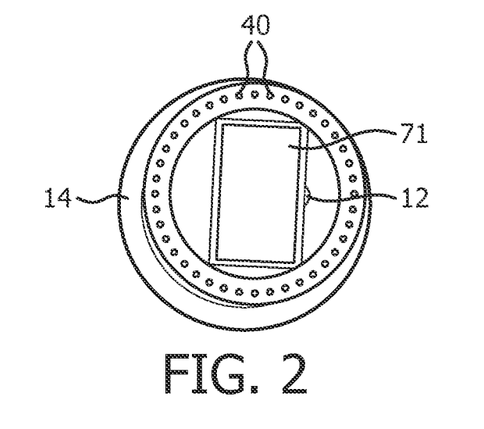
FIG. 2 is a view of the face of the 3D probe of FIG. 1 with the needle guide attached to and surrounding the distal end of the probe.
Figure 3:
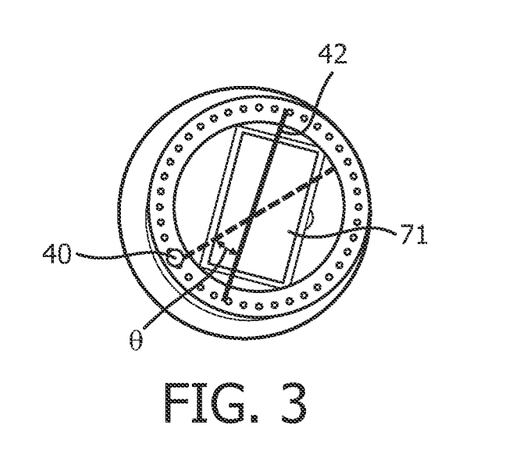
FIG. 3 illustrates a reference plane location and an insertion plane location of the probe and needle guide of FIGS. 1 and 2.

Referring first to FIG. 1, a 3D ultrasound imaging probe 12 is shown being held at its proximal (cable) end with a needle guide 14 of the present invention attached to the distal (acoustic window) end of the probe. The needle guide attaches to the probe in a fixed orientation by alignment with a distinctive feature of the probe such as its probe orientation marker. A probe orientation marker is a feature usually located on a side of the distal end of the probe which the clinician uses to relate the orientation of the probe on the subject to the orientation of the anatomy in the ultrasound image. See, for example, U.S. Pat. No. 5,255,682 (Pawluskiewicz et al.) In a constructed embodiment the probe 12 has an orientation marker formed as a projection which is aligned with a mating notch in the inner circumference of the needle guide, thereby assuring that the needle guide can be attached to the probe in only one known orientation. When properly attached the face of the needle guide is aligned with the face of the lens 71 of the probe as shown in the plan view of the face of both components in FIG. 2. The illustrated needle guide is a ring-like structure with a number of angled holes 40 located around the guide. The holes are slightly larger than the size of the needle with which the guide is intended to be used, small enough to constrain the path of insertion of the needle yet large enough to permit the clinician to move and guide the needle as it is inserted. In the illustrated needle guide there are thirty-six evenly spaced holes 40, one every 10° around the circumference of the ring-like guide. The holes are angled so that the path of an inserted needle is directed under the lens 71 and travels into the aperture of the probe. In the illustrated embodiment the holes are angled at 20° with respect to an axis normal to the face of the probe lens. The probe 12 is a 3D imaging probe which preferably has a two-dimensional array of transducer elements by which a pyramidal or trapezoidal volume in front of the lens can be scanned by electronic beam steering. Mechanically scanning 3D probes may also be used. As a needle is guided into the subject by the needle guide, its path of insertion is guided into the volumetric region which can be imaged by the 3D probe 12. FIG. 3 illustrates a reference plane 42 projecting normal to the face of the lens 71 and orthogonal to the ends of the 2D array probe. This illustration shows a hole 40 (enlarged for purposes of illustration) through which a needle can be inserted to travel along an insertion path in an imaging plane of the probe which is at an angle of e with respect to the reference plane 42.

Figure 4:
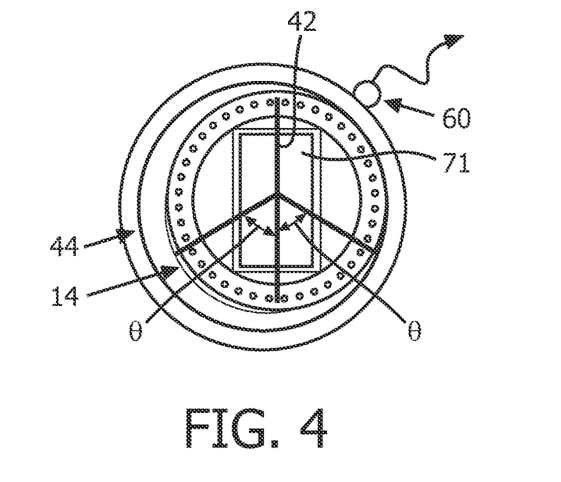
FIG. 4 shows the needle guide attached to the end of the probe with a surrounding needle position encoder and a wireless communicator.

FIG. 4 illustrates the needle guide 14 with a rotational encoder 44 that identifies the location of a hole around the guide through which a needle is inserted. When a needle is inserted through a hole at the eight o'clock position of the guide 14 in FIG. 4, the encoder identifies a scan plane at a position of e with respect to the reference plane 42 in which the needle insertion path can be imaged. If a needle is inserted through a hole at the four o'clock position, for instance, the encoder will identify a scan plane at a position of $-\theta$ in which the insertion path can be imaged. The identified scan plane is communicated to the ultrasound system operating the probe, by either a wired connection or a wireless connection such as a Bluetooth communication link 60. Power for the encoder can be provided by either a wired connection or a battery 62.

Figure 5A:
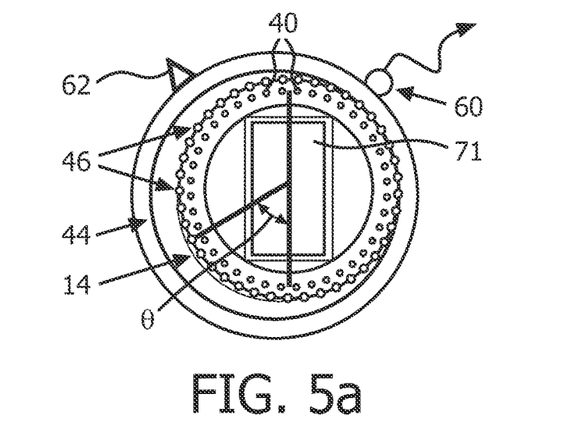
FIG. 5a illustrates a needle guide of the present invention which employs an optical needle position encoder.

The encoder can be constructed in a number of ways. One way is to use optical encoding as shown in FIG. 5a. In this embodiment there are a number of light emitters such as LEDs 46 which direct light across the holes 40 to light detectors on the other side of the holes. When a needle is inserted through a particular hole, the needle will block the light from the detector for that hole and the detector signal then identifies that particular hole and its corresponding scan plane as one through which a needle is being inserted. The ultrasound probe and ultrasound system will then image the identified scan plane and the needle being inserted in that plane. As illustrated in FIG. 5a, when a needle is inserted through a hole 40 at the eight o'clock position of the needle guide, the optical detector signal identifies scan plane θ as that of the needle insertion path.

Figure 5B:
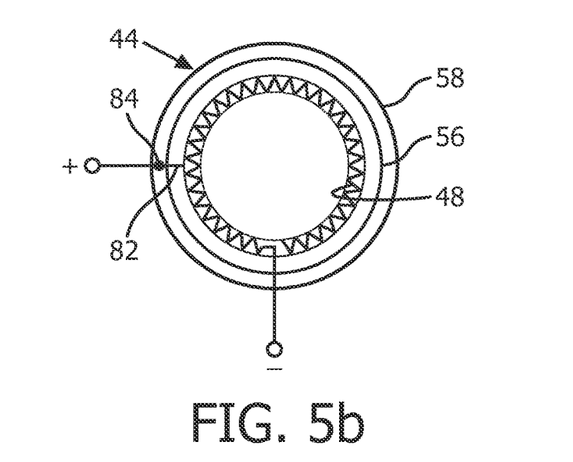
FIG. 5b illustrates a needle guide of the present invention which employs a resistive needle position encoder.

Another encoder implementation which uses a resistive encoder is illustrated in FIG. 5b. In this implementation the encoder 44 has an outer slip ring with one or more holes or grooves 84 through which a needle can be inserted. The outer slip ring 58 can be rotated around an inner ring 56 which has a resistive path 48 around the ring. The outer slip ring has a sliding contact 82 in a known relationship to the position of the hole or groove 84 of the slip ring 58 which is in electrical contact with the resistive path 48. The sliding contact and resistive path thereby operate as a potentiometer such that an electrical measurement between "+" and "−" terminals electrically connected to the sliding contact 82 and an end of the resistive path will identify the position of the hole or groove around the ring-like structure. This position information is reported to the ultrasound system to identify the plane of the needle insertion path to be scanned by the probe and ultrasound system. Multiple holes or grooves can be individually identified by connecting an additional resistance in series with a respective terminal so that the range of resistance values reported for one hole does not overlap the range of resistance values for the others.

Figure 6:
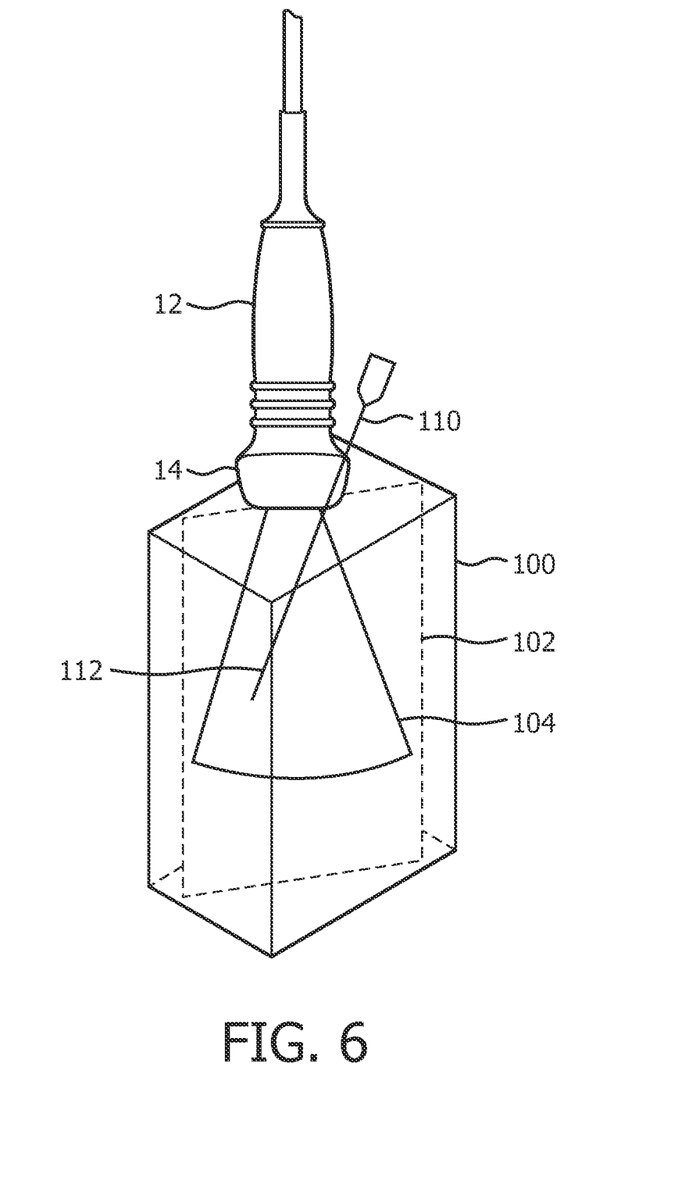
FIG. 6 illustrates the relationship between the plane of needle insertion and the location of the biplane in which the insertion plane is located in relation to the volumetric region which can be scanned by a 3D imaging probe.

FIG. 6 is an illustration of the relationships between a 3D imaging probe 12, the volume 100 which may be scanned by the probe, and a selected scan plane 102 in which the image field 104 of the probe is positioned. When a needle 110 is inserted through a hole or groove in the needle guide 14, the needle is constrained to a path which comes into view beneath the acoustic window of the probe. Since the probe is a 3D imaging probe, it is capable of scanning numerous plane orientations in the volume 100. The rotational encoder of the needle guide 14 identifies the particular hole through which the needle is being inserted, which corresponds to a particular scan plane orientation 102 that can be imaged by the 3D imaging probe. The probe 12 then images the identified scan plane orientation as illustrated by the sector scan area 104 in plane 102. The clinician can then follow the progress of the needle 110 as it is inserted along an insertion path in the sector scan area 104 until the tip 112 of the needle accesses the target anatomy.

Figure 7:
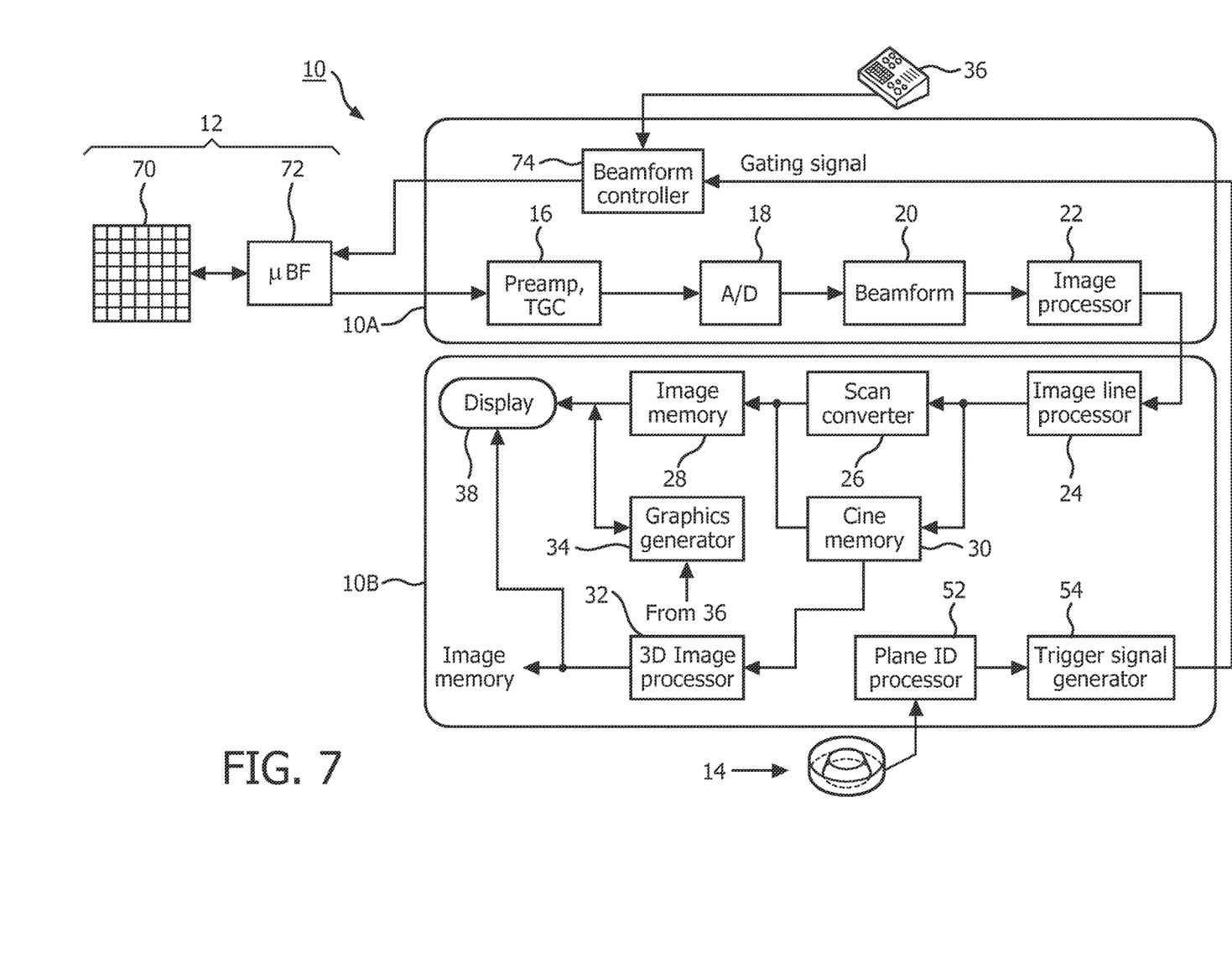
FIG. 7 illustrates in block diagram form an ultrasound system with a needle guide constructed in accordance with the principles of the present invention.

FIG. 7 illustrates an ultrasound probe, needle guide, and ultrasound system constructed in accordance with the principles of the present invention. The ultrasound system 10 is configured by two subsystems, a front end acquisition subsystem 10A and a display subsystem 10B. A 3D ultrasound probe 12 is coupled to the acquisition subsystem which includes a two-dimensional matrix array transducer 70 and a micro-beamformer 72. The micro-beamformer contains circuitry which control the signals applied to groups of elements ("patches") of the array transducer 70 and does some processing of the echo signals received by elements of each group. Micro-beamforming in the probe advantageously reduces the number of conductors in the cable between the probe and the ultrasound system and is described in U.S. Pat. No. 5,997,479 (Savord et al.) and in U.S. Pat. No. 6,436,048 (Pesque), and provides electronic steering of beams on transmit and receive for high frame rate real-time (live) 2D or 3D imaging.

The probe 12 is coupled to the acquisition subsystem 10A of the ultrasound system. The acquisition subsystem includes a beamform controller 74 which is responsive to a user control 36 and, for the present invention, a gating signal, which provide control signals to the microbeamformer 72, instructing the probe as to the timing, frequency, direction and focusing of transmit and receive beams and the plane or planes to be scanned by those beams. The beamform controller also controls the system beamforming of echo signals received by the acquisition subsystem by its control of analog-to-digital (A/D) converters 18 and a beamformer 20. Partially beamformed echo signals received from the probe are amplified by preamplifier and TGC (time gain control) circuitry 16 in the acquisition subsystem, then digitized by the A/D converters 18. The digitized echo signals are then formed into fully steered and focused beams by a main system beamformer 20. The echo signals are then processed by an image processor 22 which performs digital filtering, B mode and M mode detection, and Doppler processing, and can also perform other signal processing such as harmonic separation, speckle reduction, and other desired image signal processing.

The echo signals produced by the acquisition subsystem 10A are coupled to the display subsystem 10B, which processes the echo signals for display in the desired image format. The echo signals are processed by an image line processor 24, which is capable of sampling the echo signals, splicing segments of beams into complete line signals, and averaging line signals for signal-to-noise improvement or flow persistence. The image lines for a 2D image are scan converted into the desired image format by a scan converter 26 which performs R-theta conversion as is known in the art. The scan converter can thus format rectilinear or sector image formats. The image is then stored in an image memory 28 from which it can be displayed on a display 38. The image in memory is also overlaid with graphics to be displayed with the image, which are generated by a graphics generator 34 which is responsive to the user control 36 so that the graphics produced are associated with the images of the display. Individual images or image sequences can be stored in a cine memory 30 during capture of image loops or sequences.

For real-time volumetric imaging the display subsystem 10B also includes a 3D image rendering processor 32 which receives image lines from the image line processor 24 for the rendering of real-time three dimensional images. The 3D images can be displayed as live (real time) 3D images on the display 38 or coupled to the image memory 28 for storage of the 3D data sets for later review and diagnosis.

In accordance with the present invention the scan plane identification signal produced by the needle guide 14, which identifies the scan plane in which a needle inserted through the needle guide will pass and can be imaged, is coupled to a plane ID processor 52. The plane identification signal produced by the plane ID processor is coupled to a trigger signal generator 54 which produces a gating signal that commands the beamformer controller 74 to control the scanning of a desired scan plane, one in which a needle insertion path is located. The beamformer controller 74 controls the microbeamformer 72 to scan the desired scan plane and produce echo signals from the scanning of the desired plane which are partially beamformed by the microbeamformer and coupled to the system beamformer 20 for completion of beamformation of scanline in the desired plane. The scanlines of the plane are processed by the image line processor 24 and scan converted into a two dimensional image of the identified plane which is displayed on the display 38. The identified scan plane can be imaged as a single thin plane within the elevational resolution of the probe and system, but can also be imaged as a thick slice image of a plane thickness greater than that of a single thin plane as described in US patent publication no. US2010/0168580A1 (Thiele et al.) The use of thick slice imaging enables the needle to be continually visualized in the image even if its path of insertion varies from a perfectly straight line, so long as the path remains within the thickness of the thick slice image.

Figure 8:
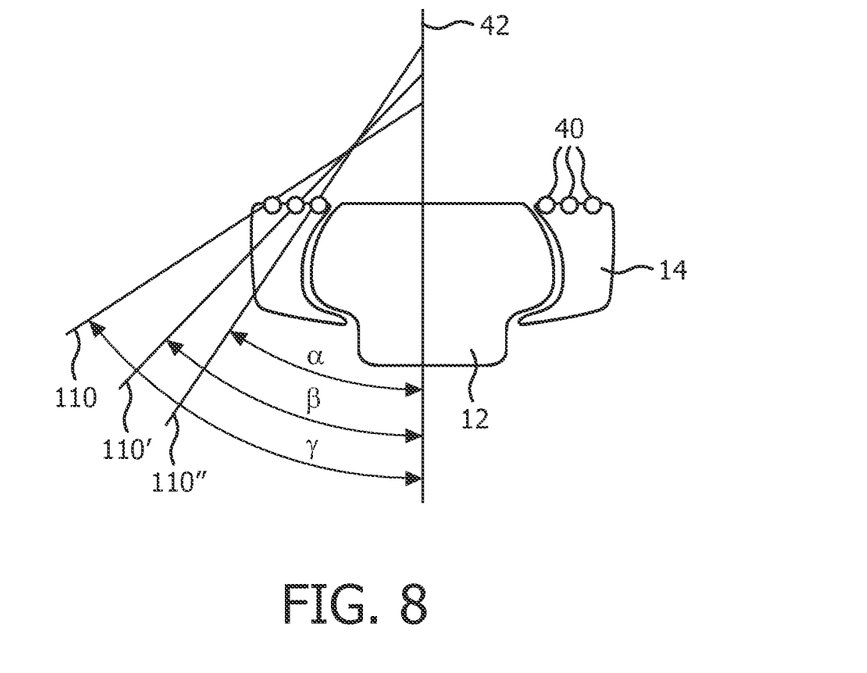
FIGS. 8 an 9 illustrate a needle guide of the present invention with multiple angles of inclination for needle insertion.
Figure 9:
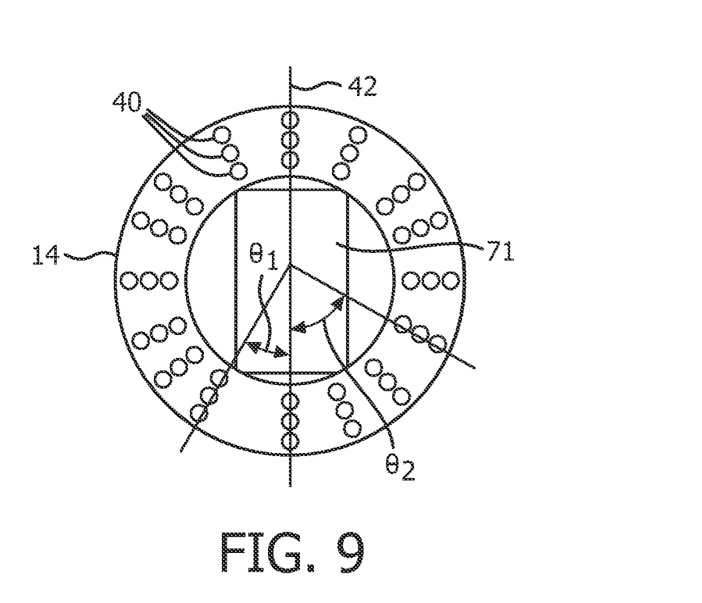

FIGS. 8 and 9 illustrate another needle guide of the present invention through which needles 110 can be inserted at different inclination angles α, β, and γ. The cross sectional view of FIG. 8 shows three needles 110, 110', and 110" inserted through different holes 40 of the needle guide which guide the needles along insertion paths inclined at angles γ, β, and α, respectively. Each set of three holes at a particular rotational position around the guide will direct the needles along an insertion path in the same scan plane, two of which, $\theta_1$ and $\theta_2$, are shown in FIG. 9 in relation to the central reference plane 42. The needle guide 14 of FIGS. 8 and 9 enable a clinician to access target anatomy at different depths below the probe while identifying the scan plane of each insertion path.

Figure 10:
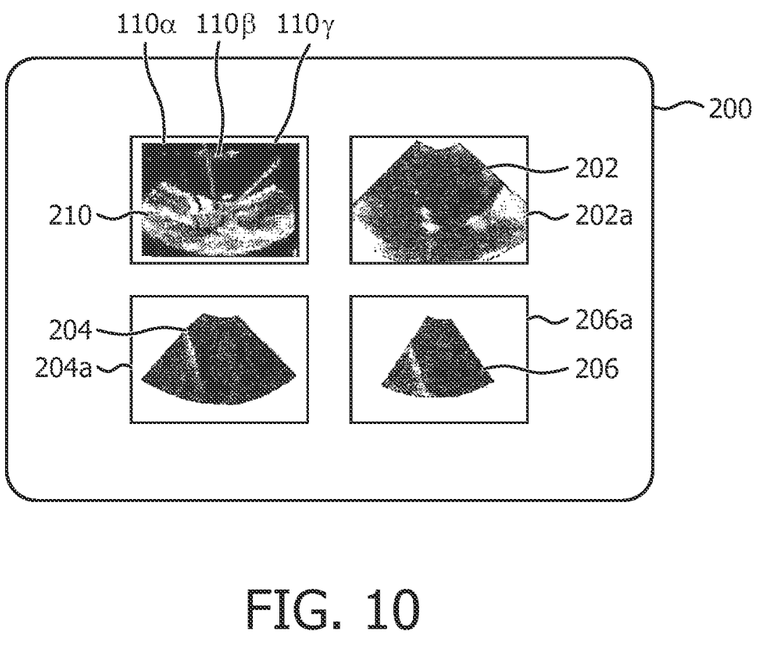
FIG. 10 illustrates an ultrasound display of multiple needles being used for a microwave ablation procedure.

In a given invasive procedure it may be desirable to access anatomy in the body with several invasive instruments simultaneously. As FIGS. 4 and 9 illustrate, multiple needles can be inserted at the same time in different identified scan planes θ1 and θ2 or +θ and −θ, for example. When two insertion paths through the guide are used, the guide will report the identity of the two different scan plane orientations to the plane ID processor, which will cause the ultrasound system 10 to alternately scan the different planes. Two different instruments may be used for microwave ablation of target anatomy, for instance, in which case the clinician will want to visually guide both ablation needles to the target so that their tips are in contact with the anatomy to be ablated. FIG. 10 illustrates an ultrasound display which shows four different images of an invasive procedure using a needle guide of the present invention. In this example three different needles, 110α, 110β, and 110γ are being used and imaged at the same time. Needle 110α is shown in ultrasound image 202 of the insertion path scan plane of needle 110*u* and the border 202*a* of this image is colored a unique color such as blue to distinguish the image of needle 110α. Identifying and coloring a needle in an ultrasound image can be performed by a segmentation technique that specifically identifies the needle in an image from its surrounding tissue as described in US patent pub. no. 2004/0002653 (Greppi et al.) and in the paper "Enhancement of Needle Visibility in Ultrasound-guided Percutaneous Procedures" by S. Cheung et al., *Ultrasound in Med. & Biol.*, vol. 30, no. 5 (2004) at pp 617-24, for example. Similarly, needles 110β and 110γ are shown in respective 2D images 204 and 206 of their insertion paths and are outlined in distinctive colors 204*a* and 206*a* such as red and yellow. Image 201 is a full 3D volumetric image of the region of the procedure which shows the target anatomy being accessed by all three needles. In the 3D image each needle is colored with its distinctive color, blue, red, or yellow, so that the clinician can easily relate each needle in the 3D image to its own 2D insertion plane image. Each 2D image plane and the full 3D volume are scanned in a time interleaved manner, with the individual insertion planes being scanned at a greater repetition rate (and hence real time frame rate of display) than the 3D image. Once the needles are in their desired positions in the target anatomy the individual 2D images can be frozen on the screen so that the full acquisition time is devoted to 3D imaging and the procedure at the target anatomy can continue to be imaged in live 3D.

An implementation of the needle guide and ultrasound system of the present invention can be assisted by other guides to help the clinician plan and carry out a needle insertion procedure, such as guiding the clinician in needle insertion to avoid hard tissues and critical anatomy as described in U.S. patent application No. 61/587,784, filed Jan. 18, 2012 and entitled "ULTRASONIC GUIDANCE OF A NEEDLE PATH DURING BIOPSY" (Kudavelly et al.) Avoidance of hard tissue in the insertion path can help prevent deflection and bending of a needle during insertion. This guidance assistance can be used to plan the insertion path prior to the procedure or to provide guidance as a needle is being inserted.

What is claimed is:
1. An ultrasonic imaging system comprising:
a 3D ultrasonic imaging probe which is capable of scanning different imaging planes of a volumetric region while the imaging probe is in a stationary position with respect to the volumetric region;

a needle guide having a plurality of needle insertion positions to guide a needle for insertion into the volumetric region through a plurality of different needle insertion planes, each of the plurality of different needle insertion planes corresponding to one of the different imaging planes, wherein the needle guide is configured to produce a plane identification signal responsive to insertion of the needle at a given one of the plurality of needle insertion positions, the plane identification signal identifying a needle insertion plane corresponding to the given one of the plurality of needle insertion positions; and an ultrasound system coupled to the probe and configured to produce, responsive to the plane identification signal, a 2D image at a selected one of a plurality of different imaging planes of the volumetric region, wherein the selected one of the plurality of different imaging planes corresponds to the needle insertion plane identified by the plane identification signal.

2. The ultrasonic imaging system of claim 1, wherein the needle guide comprises a ring-like structure which attaches to a distal end of the 3D ultrasonic imaging probe, wherein the ring-like structure includes a plurality of angled holes or grooves, each corresponding to one of the needle insertion positions.

3. The ultrasonic imaging system of claim 1, wherein the needle guide comprises a ring-like structure which attaches to a distal end of the 3D ultrasonic imaging probe, the ring-like structure comprising an inner ring which attaches to the probe and an outer sliding ring that can be rotated around the inner ring, the outer sliding ring having a hole or groove which can be selectively positioned around the inner ring by rotation of the sliding ring.

4. The ultrasonic imaging system of claim 1, wherein the needle guide comprises a rotational encoder configured to generate the plane identification signal responsive to the insertion of the needle at the given one of the plurality of needle insertion positions.

5. The ultrasonic imaging system of claim 4, wherein the rotational encoder comprises an optical encoder.

6. The ultrasonic imaging system of claim 5, wherein the plurality of needle insertion positions are defined, at least in part, by a plurality of holes or grooves located around a perimeter of a distal end of the imaging probe; wherein the optical encoder comprises a light source configured to illuminate the plurality of holes or grooves and further comprises a plurality of optical detectors associated with the plurality of holes or grooves such that one of the plurality of optical detectors is operable to produce the plane identification signal when illumination of one of the plurality of holes or grooves is obscured by the inserted needle.

7. The ultrasonic imaging system of claim 4, wherein the rotational encoder comprises a resistance encoder.

8. The ultrasonic imaging system of claim 7, wherein different ones of the plurality of needle insertion positions of the resistance encoder are associated with different resistance values.

9. The ultrasonic imaging system of claim 8, wherein the resistance encoder comprises a potentiometer.

10. The ultrasonic imaging system of claim 1, wherein at least some of the plurality of needle insertion positions are angled at different inclinations with respect to an axis normal to a face of the 3D ultrasonic imaging probe.

11. The ultrasonic imaging system of claim 10, wherein at least some of the plurality of needle insertion positions angled at different inclinations are associated with the same needle insertion plane.

12. The ultrasonic imaging system of claim 1, wherein the needle guide comprises a wireless communication link for communicating the plane identification signal to the ultrasound system.

13. The ultrasonic imaging system of claim 1, wherein the needle guide comprises a wired connection to the ultrasound system for communicating the plane identification signal to the ultrasound system and receiving electrical power from the ultrasound system.

14. The ultrasonic imaging system of claim 1, wherein the ultrasound system is configured to control the 3D ultrasonic imaging probe to scan only the identified needle insertion plane of the volumetric region.

15. The ultrasonic imaging system of claim 1, wherein the ultrasound system is configured to control the 3D ultrasonic imaging probe to scan and produce a thick slice image of the volumetric region which includes the identified needle insertion plane.

16. The ultrasonic imaging system of claim 1, wherein the 3D ultrasonic imaging probe comprises a two-dimensional matrix array transducer.

17. The ultrasonic imaging system of claim 1, wherein the ultrasound system comprises a processor configured to receive the plane identification signal from the needle guide and to control the ultrasound system to produce the 2D image at the imaging plane corresponding to the needle insertion plane identified by the plane identification signal.

18. The ultrasonic imaging system of claim 1, wherein the needle guide comprises a battery.

19. The ultrasonic imaging system of claim 2, wherein the plurality of angled holes or grooves are positioned in a circular pattern around a face of the ring-like structure.

20. The ultrasonic imaging system of claim 1, wherein the needle guide is configured to attach to the 3D ultrasonic imaging probe in a predetermined orientation with respect to the probe.

* * * * *